United States Patent [19]
Shannon et al.

[11] Patent Number: 5,549,658
[45] Date of Patent: Aug. 27, 1996

[54] FOUR-CHANNEL COCHLEAR SYSTEM WITH A PASSIVE, NON-HERMETICALLY SEALED IMPLANT

[75] Inventors: Robert V. Shannon, La Canada; Gerald E. Loeb, Northridge; Fan-Gang Zeng, Montrose, all of Calif.

[73] Assignees: Advanced Bionics Corporation, Sylmar; House Ear Institute, Los Angeles, both of Calif.

[21] Appl. No.: 328,260

[22] Filed: Oct. 24, 1994

[51] Int. Cl.$^6$ .............................. H04R 25/00; A61N 1/32
[52] U.S. Cl. ................................................ 607/57; 607/56
[58] Field of Search ................................. 607/55, 56, 57, 607/116, 137

[56] References Cited

U.S. PATENT DOCUMENTS

| | | | |
|---|---|---|---|
| Re. 32,947 | 6/1989 | Dormer et al. | 607/57 |
| 3,449,768 | 6/1969 | Doyle | 3/1 |
| 3,751,605 | 8/1973 | Michelson | 179/107 R |
| 3,752,939 | 8/1973 | Bartz | 179/107 R |
| 4,357,497 | 11/1982 | Hochmair et al. | 179/107 E |
| 4,400,590 | 8/1983 | Michelson | 179/107 |
| 4,408,608 | 10/1983 | Daly et al. | 128/421 |
| 4,516,820 | 5/1985 | Kuzma | 607/137 |
| 4,532,930 | 8/1985 | Crosby et al. | 128/419 R |
| 4,611,598 | 9/1986 | Hortmann et al. | 607/57 |
| 4,679,560 | 7/1987 | Galbraith | 128/419 R |
| 4,686,765 | 8/1987 | Byers et al. | 29/858 |
| 4,813,417 | 3/1989 | Soli et al. | 607/56 |
| 4,819,647 | 4/1989 | Byers et al. | 128/642 |
| 4,918,745 | 4/1990 | Hutchison | 455/41 |
| 5,000,194 | 3/1991 | van den Honert et al. | 607/137 |
| 5,095,904 | 3/1992 | Seligman et al. | 128/420 |

OTHER PUBLICATIONS

Loeb, "The Functional Replacement of the Ear", *Scientific American*, 252:104–111 (1985).

Loeb et al., "Design and Fabrication of an Experimental Cochlear Prosthesis", *Med. & Biol. Eng. & Comput.*, 21:241–254 (1983).

Wilson, et al., "Better Speech Recognition with Cochlear Implants", *Nature*, 352:18, pp. 236–238 (Jul. 1991).

Shannon, et al., "Mathematical and Acoustic Models of Neural Activation Patterns in Cochlear Implants", *Abstracts of the 17th Midwestern Research Meeting, Association for Research in Otolaryngology*, St. Petersburg Beach, Florida (Feb. 6–10, 1994).

(List continued on next page.)

*Primary Examiner*—William E. Kamm
*Assistant Examiner*—Carl H. Layno
*Attorney, Agent, or Firm*—Fitch, Even, Tabin & Flannery

[57] ABSTRACT

A low-cost, multichannel cochlear stimulation system utilizes a passive, non-hermetically sealed, implantable receiver/electrode array and an external wearable processor. At one end of the receiver/electrode array, positioned subcutaneously near the surface of skin above the ear, multiple receiving coils are arranged in an appropriate pattern. At the other end, which is adapted for insertion into the spiral-shaped cochlea, electrodes are spaced apart along the spiral. Each electrode is electrically connected to a respective receiving coil in a monopolar or bipolar fashion. The wearable processor senses audible sounds, converts the sensed sounds to corresponding electrical signals, and divides the electrical signals into multiple frequency bands or channels. A continuous interleaved sampling (CIS) speech processing strategy applies the processed signals of each channel to each of multiple external coils, one coil for each channel, as a series of narrow, rapid, biphasic current pulses. The external coils are aligned, using a suitable headpiece, with corresponding coils of the receiver/electrode array. The narrow CIS pulses contain sufficiently high frequency components to inductively couple the biphasic current pulses directly to the aligned implanted coils without having to modulate a high frequency carrier signal with the biphasic pulses. The induced voltage at the implanted coils causes the biphasic current pulse to appear at a respective electrode of the implanted electrode array, thereby providing electrical stimulation at the cochlea as a function of sensed audible sounds.

30 Claims, 5 Drawing Sheets

OTHER PUBLICATIONS

Loeb, et al., "Design for an inexpensive but effective cochlear implant system; recommendations for an expert panel from the 1993 Zhengzhou International Symposium on Electrical Cochlear Hearing and Linguistics", *Book of Abstracts from the International Cochlear Implant, Speech and Hearing Symposium,* Melbourne, Australia (Oct. 24–28, 1994).

Hochmair–Desoyer, et al, "An Eight Channel Scala Tympani Electrode for Auditory Prostheses", *IEEE Transcations on Biomedical Engineering,* BME–27, No. 1, Jan. 1980, pp. 44–50.

White, Robert L., "System Design of a Cochlear Implant, "*IEEE Engineering in Medicine and Biology Magazine,* Jun. 1987, pp. 42–46.

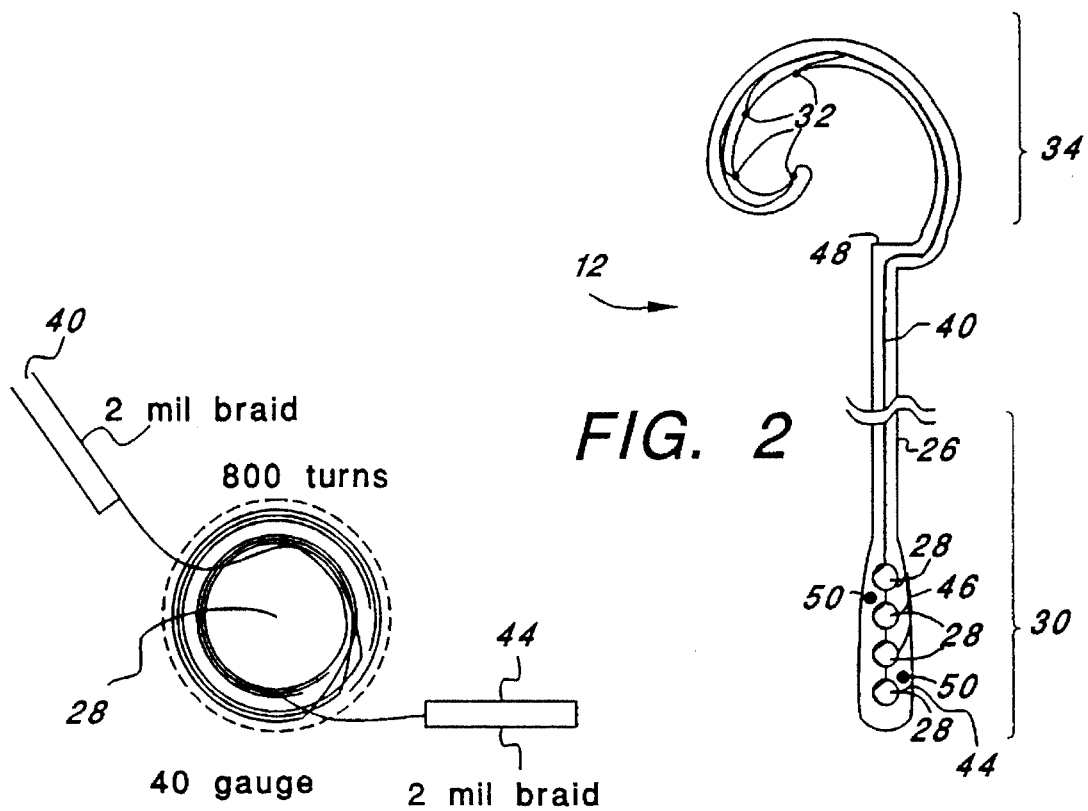
FIG. 2
FIG. 3
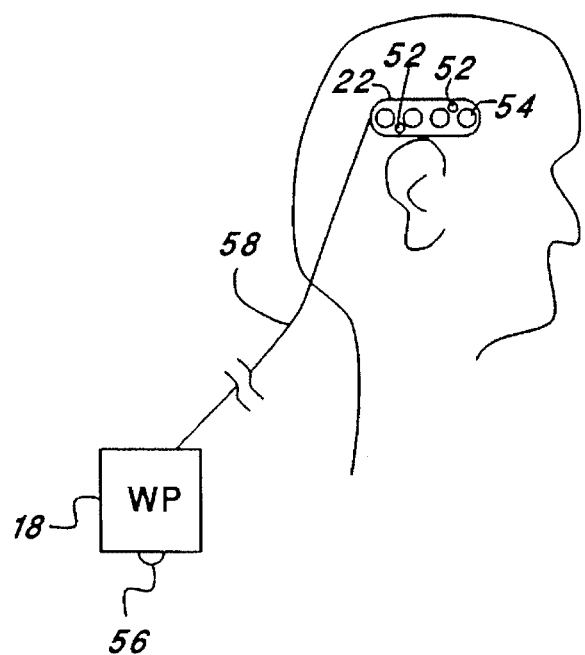
FIG. 4

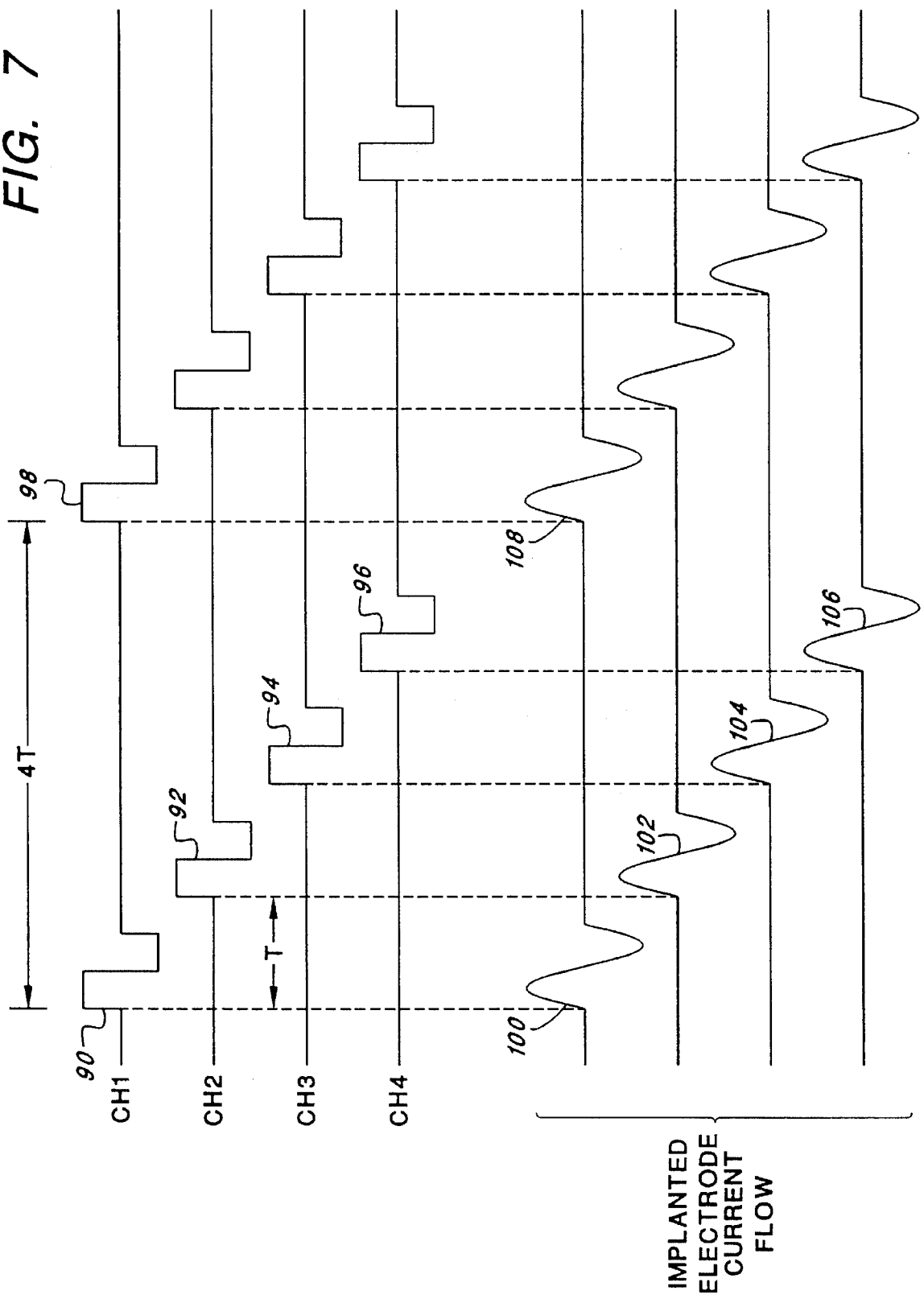

FOUR-CHANNEL COCHLEAR SYSTEM WITH A PASSIVE, NON-HERMETICALLY SEALED IMPLANT

BACKGROUND OF THE INVENTION

The present invention relates to low-cost cochlear implants, and more particularly to a low-cost cochlear implant that artificially stimulates the cochlea as a function of sensed audio signals to improve hearing of the hearing impaired.

Cochlear implant devices and systems are in worldwide use to restore useful auditory sensations to deaf patients. Such devices and systems take numerous forms, as seen, e.g., in U.S. Pat. Nos. 3,751,605; 4,357,497; 4,400,590; 4,408,608; 4,532,930; 4,9118,745; or 5,095,904, all of which typically include an external (or wearable) processor and an implanted stimulator. Such transmission requires generating a carrier signal and modulating the carrier signal with information representative of the sensed and processed sounds. The external processor includes circuitry for sensing audio sounds, processing the sensed sounds in accordance with an appropriate speech processing strategy, and transmitting a signal representative of the sensed and processed sounds to the implanted stimulator. The implanted stimulator includes appropriate electronic circuitry, powered from electromagnetic energy contained within the carrier signal transmitted from the external processor, that receives the transmitted carrier signal, extracts operating power therefrom, demodulates and decodes it, and applies an appropriate stimulation signal to one or more electrodes of an implanted cochlear electrode array. The electrodes of the array are implanted within the cochlea, and when energized cause an electrical current (stimulation pulses) to flow, in accordance with a pattern and amplitude as determined by the speech processing strategy, in order to stimulate the neurons of the auditory nerve. Such stimulation imparts to a patient the sensation of hearing. Performance of some patients who use such cochlear stimulation systems is good enough to allow conversation over the telephone.

Recent advances in speech processing strategies have demonstrated that the level of speech recognition in all implant patients may be significantly improved. See, e.g., Wilson et al., "New levels of speech recognition with cochlear implants," *Nature*, Vol. 352, pp. 236–238 (1991). Unfortunately, the high cost of present commercially available cochlear implants makes them unaffordable for many patients. What is needed, therefore, is a low-cost cochlear implant device that would allow the recent advances in speech processing strategies to be more widely used and available to deaf patients than has heretofore been possible.

A low-cost cochlear device must not achieve its low cost at the expense of patient safety. In any implanted electronic device several potential hazards exist for the patient. For example, all materials should be fully biocompatible, or otherwise insulated from direct exposure to body fluids. If toxic internal components are necessary, they must be encapsulated in an impenetrable casing (hermetically sealed) to protect surrounding tissue. All manufacturing and construction techniques must be performed in a suitable clean room or laminar flow hood to reduce the possibility of dust or other airborne contaminants from entering the fabrication materials. Further, all components used in the overall design must assure reliable operation over a long period of time, preferably for the lifetime of the patient. As the number of components within the implanted device decrease, these safety and reliability concerns can generally be kept at manageable levels. Hence, it is best for an implantable cochlear stimulator to have a low parts count.

The first goal of any auditory device, of course, is to provide the user with a reasonable level of auditory function. Like most evolving technologies, what is "reasonable" has changed in recent years as the performance of cochlear implant devices has improved. If reasonable speech recognition is defined as 20% correct or better using only sound sensed through the implant for everyday sentences or their equivalent, then a multi-channel device is necessary.

For purposes herein, "multichannel" means that stimulation may be applied to the cochlea at several physically-separated sites, each of which is selectively and independently controlled by respective electronic circuits, or "channels" in accordance with the desired speech processing strategy. It is generally agreed that having multiple channels provides improved auditory response. However, the optimal number of channels to use, particularly in view of the increased cost and complexity of the device, remains an unanswered question.

Multichannel devices should not be confused with single channel cochlear implant devices, such as is shown in U.S. Pat. No. 3,751,605, where the information contained in a single information channel is transmitted and applied to an intra-cochlear electrode. While single channel devices can be made much simpler and less costly than a multichannel device, they only provide some sound awareness and limited speech discrimination. As such, they are primarily useful only as an aid to lipreading. In contrast, present day multichannel devices provide open-set speech recognition in the 30–60% range of most patients, with some patients being able to converse over the telephone with strangers.

Likewise, multichannel devices should not be confused with simple multielectrode schemes where effectively a single channel of auditory information is applied, on a shared basis, to multiple electrodes, such as is described in U.S. Pat. No. 3,449,768. Although the '768 patent refers to its separate electrode pairs as separate "channels," they are clearly not separate channels as that term is used today to describe cochlear stimulating devices. Multi-electrode schemes driven by a single auditory channel of information, such as that depicted in the '768 patent, have long been abandoned as ineffective at producing acceptable speech recognition.

Although some patients with multichannel devices do not perform well, such should not be viewed as an indication of the failure of multichannel devices. Rather, such failure probably reflects the fact that some patients with poor nerve survival, electrode placement, or device adjustment cannot recognize speech even with multichannel implants. Thus, while there is a wide variation in performance for all patients, over 20 years experience indicates that a multichannel implant is necessary to achieve reasonable speech recognition.

Disadvantageously, the use of multiple channels significantly increases the cost and complexity of the device, particularly the implant device. Yet, as indicated above, a multichannel device is much preferred over a single channel device in order to significantly improve the level of auditory function provided by the device. Hence, it is apparent that there is a need in the art for a multichannel device that avoids the complexity and expense of existing multichannel devices, is inexpensive to manufacture and maintain, and is safe to implant and use.

A further contributor to the high cost of cochlear implant devices is hermetic sealing. Any electronic package implanted into the human body must be hermetically sealed to protect the delicate electronic components from the harsh body fluids, and to protect the patient from exposure to potentially toxic chemicals contained in the electronic components. Early cochlear implant devices were encapsulated in silicone rubber, epoxy resin and/or bone wax. These devices lasted for many months (and in some cases years), but all failed eventually because water vapor penetrated through the silicone rubber and epoxy, causing corrosion and short-circuiting of the passive components, and/or failure of the active components.

Hermetic sealing, unfortunately, is a complex technology that is still undergoing significant development efforts in related implantable industries, e.g., the pacemaker industry. Titanium or ceramic capsules are sealed with electron beam welding or laser welding or brazing. The electrical leads coming out of the capsule present a particularly difficult problem for the seal. Each lead must be fully hermetically sealed and insulated from the capsule. This is typically accomplished by conductive pins sealed to ceramic collars which are then sealed to the capsule. Electrode wires are then connected to the pins. Hermetic sealing is one of the most costly and difficult processes used in construction of modern cochlear implants. For a truly low-cost cochlear implant device to be made, either a low-cost hermetic seal must be developed, or the implant device itself must be able to function safely for long periods of time without the need for an hermetic seal.

The present invention advantageously addresses the above and other needs.

SUMMARY OF THE INVENTION

The present invention provides a low-cost multichannel, cochlear implant system that includes an external portion and an implantable portion. The external portion includes a wearable processor connected to a headpiece via a suitable connecting cable in conventional manner. A microphone senses audible sound signals and converts them to electrical signals. The electrical signals, after preliminary processing, are split into one of multiple frequency bands or channels. The signal in each frequency band is further processed in order to generate a signal that preserves the loudness relations within and between the speech sounds of that band. The signal thus processed is then pulse modulated using a continuous interleaved sampling (CIS) strategy. The modulated processed signal is then applied, via the connecting cable, to respective coils for each band or channel located in the headpiece.

The implantable portion of the cochlear implant system includes a passive, transcutaneous implantable receiver integrally connected to a cochlear electrode array. Electrically, the implantable receiver includes only a receiving coil for each channel, which coil has at least one side electrically connected to a respective electrode of the electrode array. Typically, the other side of the coil is connected to a common reference electrode, thereby providing monopolar stimulation between each electrode and the common reference electrode. In other embodiments, the other side of the coil may be connected to another electrode of the electrode array, thereby providing bipolar stimulation between the two sides of the coil. In a preferred four-channel configuration, the implantable receiver/electrode array simply comprises four implantable coils, each having one end thereof electrically connected to a respective electrode of the cochlear array, and the other end electrically connected to the common reference electrode.

Advantageously, because there are no active components in the implantable portion, nor even any passive components except for the wire from which the coils and electrodes are made, there is no need for hermetic sealing. The wire is usually made from biocompatible materials, and is thus of medical grade. The wire may be multi-stranded for flexibility and reliability, but such is not necessary. The wire is typically insulated with a suitable biocompatible insulating material, such as Teflon. The electrode ends of the wire may be made as balls that are formed by flaming the end of the wire. In order to reduce cost, the coil part of the implantable portion may be made from one type of wire, e.g., copper, and the lead/electrode part of the implantable portion may be made from another type of wire, e.g., Pt—Ir, that is welded to the coil wire. Alternatively, both the coil and the lead/electrode part may be made from one continuous type of wire. The balls, wire and coils are mounted in a carrier of silicone rubber (Silastic) to ensure reliable contact spacing and to impart surgical handling properties for insertion. The large surface area on the balls advantageously produces a low electrode impedance. Such low impedance, in turn, reduces the voltage and power that must be coupled across the coil pairs.

The cochlear electrode array is inserted into the cochlea using a special insertion tool of the type described in U.S. Pat. No. 4,819,647. In one embodiment, the electrode contacts are cast into the silicone rubber carrier in a pre-formed shape that matches the basal turn of the cochlea. The electrode array typically has a mechanical memory for the coiled shape. The electrode carrier is straightened prior to insertion, and as the carrier is inserted it resumes its coiled shape, forcing the electrode contacts to hug the inner radius of the basal turn, along the modular wall of the cochlea.

Not all embodiments of the invention require the carrier to assume a spiral shape. In order to reduce costs, which is an important aspect of the present invention, the spiral design of the array may also be replaced with a less-expensive "straight" design. Such straight design still employs a flexible carrier, e.g., silicone rubber, that would allow the distal end 34 of the array 12 to be inserted into the cochlea. Once inserted into the cochlea, such straight array would of course be held in a spiral shape by the cochlea. However, the individual electrodes would not necessarily hug the inner radius of the basal turn along the modular wall of the cochlea, as they would if a spiral shaped electrode with mechanical memory were employed. But, such electrode positioning may not be required for all patients.

The implanted coils are held by the carrier of silicone rubber in a particular pattern, or spaced relationship. Such coils are also implanted near the surface of the skin, above or near the ear. One or more permanent magnets, or magnetic pieces, may be centered within or near one or more of the coils. Such permanent magnets or pieces serve as an alignment guide for corresponding coils of the external headpiece. That is, one or more permanent magnets are also included in the external headpiece such that when the headpiece magnets are aligned with the implantable magnets or magnetic pieces, respective coils in the headpiece are also aligned and held in place with corresponding ones of the implanted coils.

In use, the external processor generates electrical signals representative of the audible sounds sensed by the microphone. Such signals are processed, in accordance with the CIS strategy, resulting in a sequential series of biphasic stimulation pulses being applied to coils held in the headpiece as a function of the auditory information of each channel. The headpiece coils, when properly aligned, are inductively coupled with the implanted coils. Hence, the biphasic stimulation pulses applied to the headpiece coils are inductively coupled to the implanted coils, causing a small, but perceptible, biphasic electrical current to flow between the electrode of the coil and the reference electrode (monopolar stimulation), or between the two electrodes of the coil (bipolar stimulation). Such stimulation activates appropriate neurons of the auditory nerve, thereby imparting to the patient the sensation of hearing. Significantly, the narrow biphasic pulses may be directly coupled to the implanted coils without the need for generating and modulating a carrier signal. The absence of a carrier signal greatly reduces the complexity, and hence the cost, of both the external processor and the implanted receiver/electrode array.

It is a feature of the invention to provide an inexpensive cochlear stimulation system that provides the best combination of reliability, low cost and robust medical properties for widespread application.

It is another feature of the invention to provide such a cochlear stimulation system wherein the implantable portion thereof need not be hermetically sealed, is made from biocompatible materials, and has a usable life that is at least as long as the expected life of the patient within whom it is implanted, thereby requiring only one surgical implantation.

It is an additional feature of the invention to provide an inexpensive cochlear stimulation system that utilizes the frequency content of brief biphasic pulses generated in multiple channels of a CIS processing strategy to inductively couple such pulses through the skin of a patient to an implanted coil with reasonable efficiency. Such pulses are then used directly as a stimulating signal at electrodes connected to the implanted coil without the need for intervening implanted electrical or electronic circuitry.

It is yet a further feature of the invention to provide, in one embodiment thereof, a low cost, reliable, cochlear stimulation system that has widespread application in underdeveloped areas, requiring minimal medical supervision and attention once implanted.

It is still another feature of the invention to provide a low-cost, four-channel cochlear stimulation system that utilizes a completely passive, non-hermetically sealed, implantable electrode array having four electrodes, four receiving coils, and a reference electrode, made from a single type, or at most two types, of metal(s), carried in a carrier of silicon rubber, one end of which is pre-formed in a spiral to match the basal turn of the cochlea, with the four electrodes being spaced apart along the inner radius of the spiral.

BRIEF DESCRIPTION OF THE DRAWINGS

The above and other aspects, features and advantages of the present invention will be more apparent from the following more particular description thereof, presented in conjunction with the following drawings wherein:

FIG. 2 shows a side view of a passive implantable cochlear electrode/coil assembly made in accordance with the present invention, with the electrode end of the assembly being formed in the general spiral shape of the basal turn of the cochlea, and with the coil end of the assembly maintaining the coils in a fixed spaced relationship relative to each other;

FIG. 3 illustrates a coil included within the electrode/coil assembly of FIG. 1;

FIG. 4 depicts the positioning of the headpiece assembly on a patient over an area where the coil end of the implantable electrode/coil assembly has been implanted;

FIG. 7 depicts the concept of continuous interleave sampling (CIS) as a preferred type of speech processing strategy for use with the present invention.

Corresponding reference characters indicate corresponding components throughout the several views of the drawings.

DETAILED DESCRIPTION OF THE INVENTION

Figure 1:
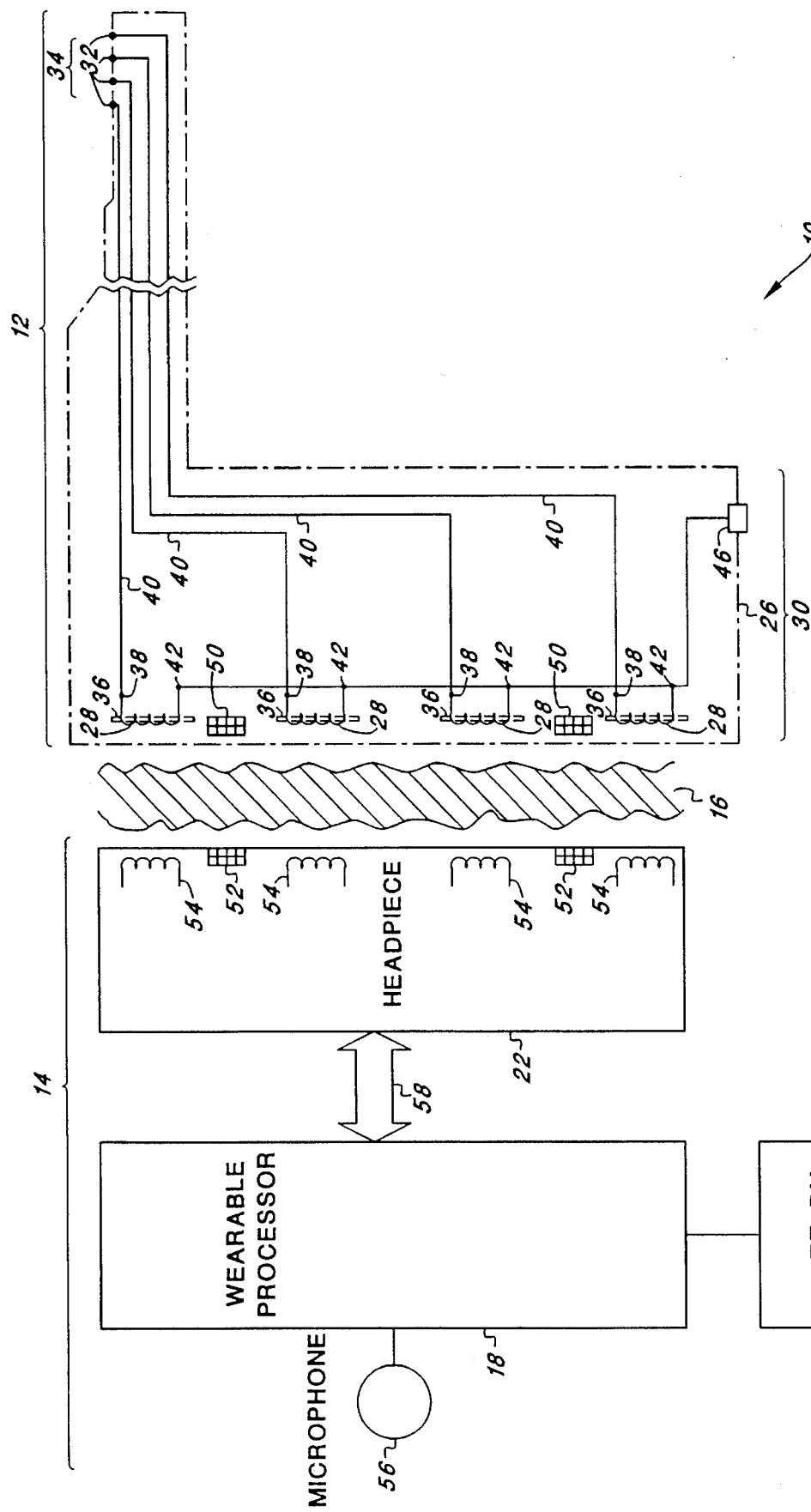
FIG. 1 is a functional block diagram of a low-cost, four channel, cochlear stimulation system made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

The goal of the present invention is to provide a low-cost cochlear implant device that safely provides a reasonable level of auditory function. A threshold determination for such a device is the number of channels that the device should include.

As the number of channels decreases, the ability of the system to provide a reasonable level of auditory function also decreases. Yet, as the number of channels increases, the size, complexity and expense of the device increases. It does not appear, at least the data is not conclusive, that a corresponding increase in auditory function is achieved as the number of electrodes and the number of channels increases to a higher number, e.g., greater than four processing channels and more than eight electrodes. That is, the test data from patients with all multichannel cochlear implants are similar, even though some devices have six electrodes and four processing channels and others have 22 electrodes and 5 processing channels. While the reasons for the similarity are not fully understood, experiments show that reasonable performance is achieved with as few as four channels. That similar performance is achieved regardless of the number of electrodes and channels used appears to demonstrate the processing power of the human brain responding to aberrant patterns of neural activity originating in the cochlea.

All existing implant processors have inherent limitations in terms of the patterns of nerve activity that they can represent. The similarity of performance achieved with such processors thus probably represents the pattern recognition of the central auditory system when confronted with equally unnatural patterns of peripheral nerve activity. It has been shown, using an acoustical model, that four channels should be adequate to provide adequate or functional levels of speech recognition if all other conditions are optimal. See, Shannon et al., "Mathematical and acoustic models of neural activation patterns in cochlear implants," Assoc. Res. Otolaryngol, p. 143 (1994).

Thus, four channels should be adequate for patients with good nerve survival and an electrode that is well-placed within the scala tympani. However, four channels, may not be adequate for patients with poor nerve survival and/or poor electrode placement. Hence, with poor nerve survival and/or poor electrode placement, it is possible that even higher numbers of electrodes and processing channels would be insufficient to provide such patients with good word recognition without lipreading. While more than four processing channels should theoretically provide more spectral information, and thus better performance, the physical size and cost of design complexity, manufacture, and maintenance increases substantially with the number of channels.

For purposes of the present invention, four channels is the preferred number of channels because it represents a good compromise between the cost and acceptable speech recognition performance in most patients. It is to be understood, however, that less than four channels, e.g., three channels, or more than four channels, e.g., five, six, seven or eight channels, may be used in some situations and with some patients.

Referring to FIG. 1, a functional block diagram of a low-cost, four channel, cochlear stimulation system 10 made in accordance with the present invention is shown. The system 10 includes a passive, non-hermetically sealed, implantable receiver/electrode array 12, and an external processing unit 14. The array 12 is made for subcutaneous implantation, below the skin 16 of the patient. The external processing unit 14 is made to be worn or carried externally (not implanted). The external unit includes, as explained more fully below, a wearable processor 18, powered by a suitable battery 20, and a headpiece 22.

The implantable receiver/electrode array 12 forms a key element of the low-cost stimulation system 10 of the present invention not because of what it contains, but because of what it does not contain. Unlike multichannel implantable cochlear stimulators of the prior art, which have always included electronic circuitry (which must be hermetically sealed) for receiving, processing and generating the stimulation signals that are used, the receiver/electrode array 12 of the present invention includes only wires, formed as coils or electrodes, a suitable carrier to hold and position the wires, and appropriate alignment elements to help align the external headpiece 22 therewith. In some situations, a bobbin, or equivalent means, may also be used as an element on which the wire can be would to form the coils. All such elements are completely passive, may be selected to be biocompatible, and thus no hermetic sealing is required. Hence, it is seen that the cost of the array 12 is significantly reduced over that of prior cochlear implant devices.

More particularly, as seen electrically in FIG. 1, and mechanically in FIG. 2, the implantable receiver/electrode array 12 includes an elongate silicone rubber carrier 26 in which is embedded a plurality of coil assemblies 28 at a proximal end 30 of the carrier and a corresponding plurality of electrodes 32 at a distal end 34 of the carrier. The distal end 34 of the carrier may be formed in the shape of a spiral to match the basal turn of a human cochlea. The plurality of electrodes 32 are spaced apart along an inner radius of the spiral.

The proximal end 30 of the carrier 26 holds the plurality of coil assemblies 28 in a predetermined pattern. Each coil assembly 28 is made from a sufficient number of turns, e.g., 800 turns, of 40 gage (AWG) insulated Pt/Ir (90/10) wire, or other suitable wire, wound on a disc-shaped Teflon bobbin 36. The bobbin 36 is shaped to form the resulting coils as pancake coils, having an approximate diameter of 1.2 cm, and a thickness of 0.6 cm. The Pt/Ir wire (or other wire) is used for the coil because of its biocompatibilty.

Still referring to FIGS. 1 and 2, but with reference also to FIG. 3, a first end 38 of the 40 gage Pt/Ir biocompatible wire of each coil assembly 28 is bonded to a second biocompatible wire 40. The second wire may also be made from Pt/Ir (90/10), or may be made from another suitable biocompatible material, as discussed below. The second wire 40 may be a braided wire with each braid having a nominal diameter of 2 mils. The second wire 40 extends the length of the elongate carrier 26 inside of the carrier to a respective electrode 32 at the distal end 34 of the carrier.

A second end 42 of the biocompatible wire of each coil assembly 28 is similarly bonded to a third biocompatible wire 44. This third wire 44 is also preferably a braided wire made from Pt/Ir (90/10), but may also be made from another suitable biocompatible material. Each braid has a nominal diameter of 2 mils. Typically, it extends less than half of the length of the elongate carrier 26 to a common electrode 46, exposed at the surface of the carrier 26.

It should be noted that in some configurations the second wire 40 and the third wire 44 need not be separate wires from the wire of the coil assembly 28. That is, one end of the wire used to form the coil assembly may pass through the body portion of the carrier 26 and end at the electrode 32, with a ball electrode, as described below; with the other end of the wire used to form the coil assembly passing through the carrier 26 to the reference electrode 46. Such single-wire construction avoids a joint between the coil wire and the second wire 40 and the third wire 44. In practice, however, the coil wire will typically be a much smaller wire (smaller diameter) than the second wire 40 or the third wire 44, thereby allowing the coil assembly to have a sufficient number of turns and still maintain a reasonably small physical size. Further, there are some cost benefits, described below, to having the coil wire be one type of relatively inexpensive wire, and the electrode ends to be of another type of wire.

Each electrode 32 at the distal end 34 of the carrier 26 comprises a ball of approximately 0.5 mm diameter. Such ball may be formed by simply flaming the distal end of the second biocompatible wire 40, and positioning the ball within the carrier so that a portion thereof is exposed through the surface of the carrier. The ball electrodes are positioned within the silicone rubber (Silastic) carrier 26 to ensure reliable contact spacing and to facilitate surgical handling properties for insertion into the cochlea. The large surface area of the balls advantageously produces a low electrode impedance, and thus a low compliance voltage is all that is required to drive a charge (current flow) across the electrode/fluid interface.

The reference or common electrode 46 may be made by simply flaming the ends of the wires 44 to form balls, and then positioning the balls of each wire in the same general area on the surface of the carrier 12. Alternatively, the ends of all four wires may be welded together, e.g., flamed at the same time, effectively welding all four ends together in one large ball. Such large ball may then be formed into a desired shape, e.g., flattened, as needed. When implanted, it is preferred that the common electrode 46 be in electrical contact with the temporalis (a fan-shaped muscle situated at the side of the head).

The bonding between the 40 gage wire of the coil assemblies, and the braided wires 40 and 44, is preferably achieved by welding. The weld point between the 40 gage wire and the 2 mil braided leads is preferably reinsulated and strain relieved. Such can be accomplished by the silicone rubber carrier 26 in which the wires and joint are embedded.

As indicated above, the same type of metal may be used for the coil as well as the second wire 40 (forming the stimulating electrode 32) and the third wire 44 (forming the reference electrode 46). When the same metal is used for the electrodes, wires, and coils, there is no battery effect caused by the use of different metals, reducing the possibility of corrosion of the wires. When the same metal is not used for the electrodes, wires and coils, there may be a battery effect. However, such battery effect may be balanced by having two identical junctions where the coil wire is joined to the second wire 40 and the third wire 44. That is, if the coil wire is stainless steel (which is much less expensive that Pt/Ir), and the second and third wires are Pt/Ir, then the junction of the second wire 40 to the coil (from Pt/Ir to stainless steel) may serve as the positive battery terminal, and the junction of the coil with the third wire 44 (from stainless steel to Pt/Ir) may serve as the negative battery terminal. Other biocompatible metals (or even non-biocompatible metals that are appropriately encased in silicone rubber, Teflon, or other biocompatible insulating materials, and distant from the exposed electrode end of the array, where body fluids will eventually invade) may also be used within the invention. For example, copper wire may be used for the implanted coils, and Pt/Ir wire may then be used for the electrodes. The use of copper wire for the coils is relatively inexpensive, thereby helping to keep the overall cost of the implanted receiver/electrode array 12 low. Gold wire (or a gold-alloy wire) may also be used within the array 12, as gold is usually less expensive than platinum. Any metal that provides the desired electrical properties and can be obtained at a relatively modest cost may thus be used within the array.

It is noted that the carrier 12 may be made from other biocompatible materials, other than silicon rubber, as such materials are developed and/or made available.

The receiver/electrode array 12 of FIGS. 1 and 2 provides monopolar stimulation, i.e., the current flow occurs between one of the electrodes 32 and the reference or common electrode 46. Advantageously, a well-positioned monopolar electrode 32 produces selective stimulation equal to that achieved using a bipolar configuration, but with a lower current and voltage. To achieve the desired selectivity, the monopolar electrode 32 must be positioned along the modular way of the scala tympani, adjacent to the spiral ganglion. To reliably obtain such placement of the electrodes 32, they are (as indicated above) cast into the silicone rubber carrier 26, which carrier may be pre-formed in the shape of the basal turn or spiral of the cochlea. The electrodes 32 are then positioned and equally spaced along the inner radius of the spiral, starting with the first electrode at or near the distal tip and preceding (as depicted in FIG. 2) with the last electrode being at about 200–220° counter-clockwise from the first (relative to the center of the spiral).

Alternatively, as mentioned previously, ball electrodes may be placed on both ends of the coil wire, with such electrodes then being positioned at the distal end 34 of the carrier to form a bipolar cochlear electrode array.

In one embodiment of the invention, the distal end 34 of the array 12 has a mechanical memory to impart the coiled (or spiral) shape. The array is straightened prior to insertion in the cochlea. As it is inserted, it resumes its coiled shaped, forcing the electrodes 32 to hug the inner radius of the basal turn, along the modular wall.

In order to reduce costs, other embodiments of the invention replace the mechanical-memory-shaped spiral design of the array 12 with a less-expensive "straight" design. Such straight design employs a flexible carrier, e.g., silicone rubber, that allows the distal end 34 of the array 12 to be inserted into the cochlea, in conventional manner. Once inserted into the cochlea, such straight array assumes the spiral shape of the cochlea. However, the individual electrodes may not necessarily hug the inner radius of the basal turn along the modular wall of the cochlea, as they generally would if a spiral shaped electrode with mechanical memory were employed. Preliminary data suggests that at least some implant patients are able to achieve a high level of speech recognition when the CIS strategy is employed even without a spiral shaped electrode. If further testing bears out such data, even if only for some patients, then the mechanical-memory-spiral-shaped electrode array becomes an option that is not needed for all patients.

A final element included in the implantable receiver/electrode array 12 is one or more, preferably two, alignment elements or pieces 50. Such alignment elements 50, in the preferred embodiment, comprise a permanent magnet, such as a ceramic magnet, e.g., a Zirbidium-Cobalt, rare-earth magnet. Alternatively, a ferromagnetic plate may be used that is attracted to a permanent magnet 52 within the headpiece 22 (FIG. 1). Other types of alignment elements, other than magnetic, may also be used, such as optical or electromagnetic alignment devices and methods, or mechanical appliances worn on the head.

When the spiral-shaped electrode array 12 is used, the method of making it so that it assumes the desired spiral shape may be similar to that described in U.S. Pat. Nos. 4,686,765 and 4,819,647, incorporated herein by reference. Further, an insertion tool has been designed to hold the straightened electrode carrier in preparation for insertion. Such an insertion tool is fully described in allowed U.S. patent application Ser. No. 07/999,461, filed Dec. 29, 1992, incorporated herein by reference. To facilitate such insertion, and use of the insertion tool, a right angle 48 (FIG. 2) is offset in the silicone rubber carrier 26 at the point of full insertion. The distal end is straightened as it is retracted into a tube of the insertion tool. The tip of the tool is placed on the round window cavity of the ear, or in a cochlear fenestration. Depressing a plunger of the tool inserts the electrode array (distal end 32) into the cochlea reliably and reproducibly, with the offset angle 48 serving as a mechanical stop for the insertion. Use of the tool thus simplifies the electrode array insertion process, and reduces inter-surgeon variability in the insertion position, angle and potential insertion trauma.

The simplicity of the implantable receiver/electrode array 12, including its low parts count, advantageously allows its continued use over a long period of time, e.g., over the life of the patient, without the need for replacement, maintenance, or other attention.

The external processing unit 14 includes, as briefly indicated above, a wearable processor (WP) 18 and a headpiece 22, shown in both FIG. 1 and FIG. 4. The headpiece 22 is electrically connected to the WP 18 via a connecting cable 58. The function of the external processing unit 14 is to sense speech signals, or other audible sounds, convert such signals to appropriately processed electrical signals, and couple the electrical signals into appropriate channels of the implantable array 12 where they function as an electrical stimulus within the cochlea, stimulating appropriate neurons of the auditory nerve, and thereby imparting the sensation of hearing to the user.

The WP 18 senses speech signals using a microphone 56, which may be conventional. The microphone 56 converts the speech signals to an electrical signal, which electrical signal is processed as described below. The processed signal is then applied to one of four external coils 54 included within the headpiece 22. When proper alignment exists between the headpiece 22 and the implantable array 12, each of the four external coils 54 is inductively coupled to a corresponding one of the implantable coil assemblies 28. Thus, an electrical pulsed signal appearing at a given one of the external coils 54 is inductively coupled to the corresponding implanted coil assembly 28. Such pulsed signal thus generates a small voltage between the common electrode 46, connected to one side of the implanted coil assembly 28 via the wire 44, and the electrode 32, connected to the other side of the implanted coil assembly 28 via the wire 40. Such voltage causes an electrical current to flow through the conductive media (body tissue) that lies between these two electrodes, thereby producing the desired electrical stimulus.

To achieve the desired alignment between the headpiece 22 and the implantable array 12, the headpiece 22 includes at least one, and preferably two, alignment elements 52. As indicated above, such alignment elements 52, in the preferred embodiment, comprise Zirbidium-Cobalt, or other rare-earth, ceramic, permanent magnets that magnetic ally align with similar magnets or magnetic elements within the implantable array 12. The strength of the magnetic attraction is adjusted, as required, by controlling the size and position of the external magnets 52. Too much force can interfere with blood flow and produce flap necrosis, while too little force may result in the headpiece falling off under normal activities.

The coupling of the signals from the external coil 52 to the implanted coil assembly 28 is one of the most critical elements of the design of the cochlear stimulation system 10. Such coupling is what dramatically increases the cost in hermetically sealed systems, and in which acceptable compromises must be made to avoid hermetic sealing. The present invention achieves the necessary coupling through the use of the four coil assemblies 28 in the implantable electrode array 12. Such coils are untuned passive coils, and as such, will transmit a brief biphasic pulse with adequate fidelity. Hermetic sealing is not required because there are no connections or internal components to fail.

One disadvantage of passive coil transmission as is used with the present invention is that the coupling efficiency, and thus the level of the signal presented to the electrode, is highly dependent on the spacing between the transmitting and receiving coils, i.e., the spacing between the external coils 54 included in the headpiece 22 and the coil assemblies 28 included within the implantable array 12. Such spacing is determined by the thickness of the skin 16 of the individual patient and in the alignment of the coils. The alignment of the coils is optimized as described above. The skin thickness will vary somewhat from patient to patient. It is recommended, therefore, that during implant of the array 12, the skin flap that is placed over the proximal end 30 of the implantable array 12 be thinned down to the bottom of the hair follicles. Such procedure will keep the skin thickness to a minimum. Suitable signal strength adjustments may then be made in the WP 18, after implant, to compensate for individual variations in skin thickness.

One of the key aspects of the invention is the use of the biphasic pulses in a fast CIS strategy. Such biphasic pulses have a frequency content that is sufficiently high to permit the pulses to be inductively coupled, through a layer of skin, from the external coil 54 to the implanted coil 28 with reasonable efficiency. As a result, there is no need in the invention to generate and modulate a high frequency carrier signal (to carry information from the external unit to the implanted unit) as has been required in prior art devices that employ inductive coupling as a data link. The absence of a carrier signal further simplifies the invention and keeps its cost low. Such inductively-coupled link, through the use of two or more of such pairs of aligned coils (one external and one implanted), thus makes possible various multichannel embodiments of the invention.

Figure 5:
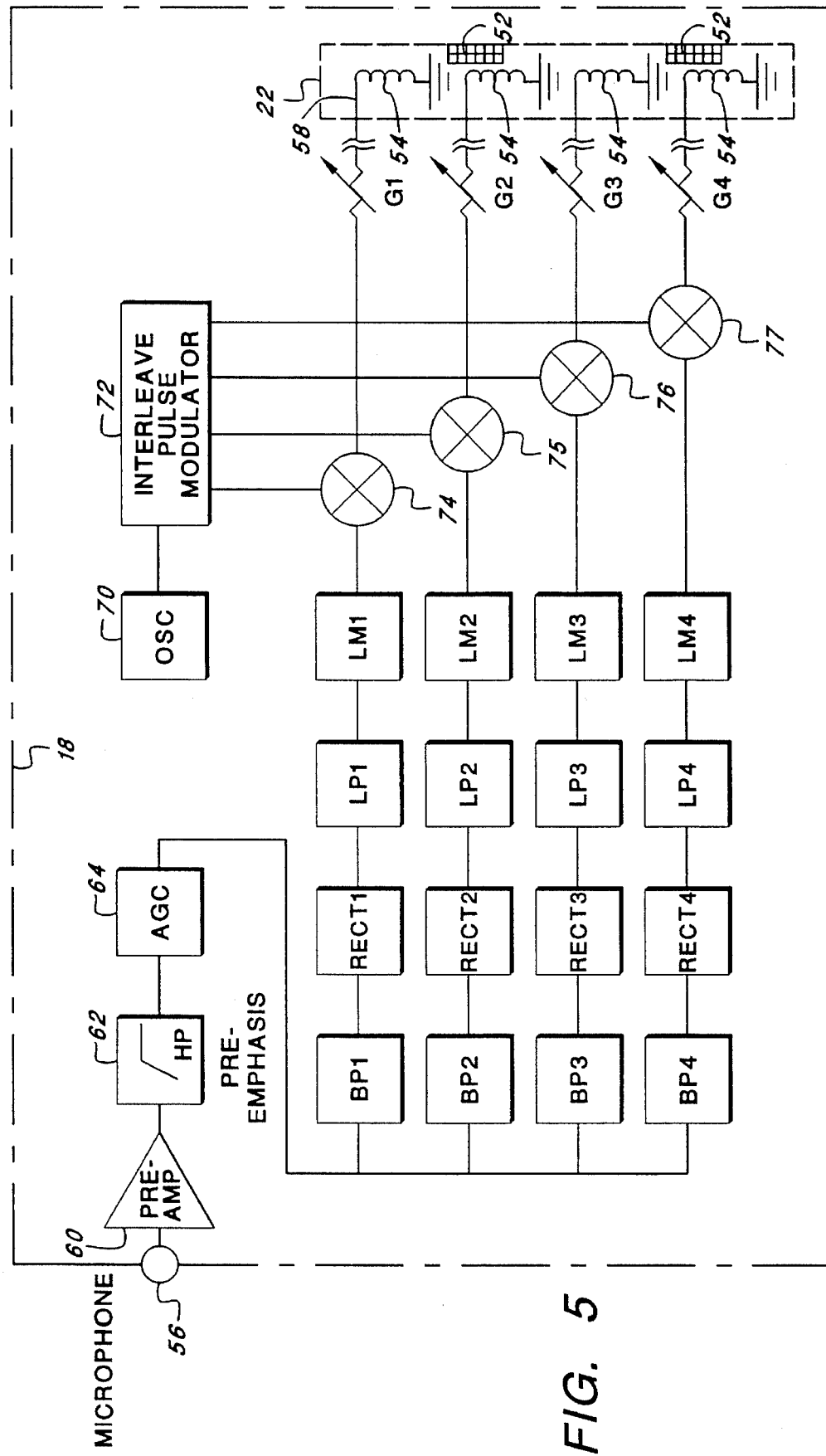
FIG. 5 is a block diagram of the external processor and headpiece portions of the cochlear stimulation system of FIG. 1.

Turning next to FIG. 5, a functional block diagram of the WP 18 and the headpiece 22 is shown. As seen in FIG. 5, the WP 18 includes a microphone 56. The microphone converts audible sounds, e.g., speech signals, into electrical signals as is known in the art. Such electrical signals are then amplified using a suitable preamplifier 60. The preamplified signal is then passed through a pre-emphasis filter 62. The pre-emphasis filter 62 is effectively a high-pass filter having a cut-off frequency of around 1200 Hz and a 6 dB/octave slope. Such slope causes the low frequency signals, i.e., those below the cut-off frequency, to be attenuated more than high frequency signals. The lower the frequency below the cut-off frequency, the more the attenuation. The net effect is to equalize the energy content of the amplified signal across the full spectrum because the incoming speech signal generally contains increased energy in the lower frequencies.

An automatic gain control (AGC) circuit 64, which may be of conventional design, then adjusts the overall signal level to compensate for differences in loudness of different speaker's voices or different distances of the speaker from the microphone 56. Such AGC circuit typically uses a rapid attack time of about 5 msec and a slow release time of around 200 msec to ensure that rapid transients will not overstimulate the listener and that soft sounds will not be lost. In combination, the microphone 56, preamplifier 60, pre-emphasis filter 62 and AGC circuit 64 may be functionally viewed as microphone means for generating an electrical signal representative of sensed audible sounds. Alternatively, for some applications, just a microphone and a preamplifier could be considered as a microphone means that generates electrical signals representative of sensed speech.

The full-band signal thus received and processed by the microphone means (e.g., the microphone 56, preamplifier 60, pre-emphasis filter 62 and AGC circuit 64) is then divided into four frequency bands by respective bandpass filters BP1, BP2, BP3 and BP4. In the preferred embodiment, the filter BP1 has a frequency band of from 100–700 Hz; BP2 has a frequency band of from 700–1400 Hz; BP3 has a frequency band of from 1400–2800 Hz, and BP4 has a frequency band of from 2800 Hz to about 5600 Hz. These frequency bands correspond roughly to the natural acoustic tuning frequencies of the intact cochlea at the locations corresponding to the intended placement of the electrode contacts when the electrode array is inserted to its full intended depth within the cochlea.

Once divided into the four frequency bands or channels, appropriate speech processing means are used to process each of the plurality of frequency band signals in accordance with a prescribed speech processing strategy. Each band is processed in the same manner.

In the preferred embodiment, as shown in FIG. 5, the processing of the signal in each channel includes first subjecting the band-limited signal to a rectifier circuit, RECT1, RECT2, RECT3 or RECT4, followed by a low-pass filter LP1, LP2, LP3, or LP4. The combination of a rectifier circuit (which may be either a full or half wave rectifier circuit) followed by a low pass filter effectively derives the instantaneous envelope of the speech (or audio) signals in that band. The preferred low-pass filter cut-off frequency for the filters LP1–LP4 is about 200 Hz.

After deriving the instantaneous envelope signal of the speech signals in each channel, available at the output of each of the low-pass filters LP1, LP2, LP3 and LP4, the envelop waveform is then mapped from acoustic amplitudes to electrical amplitudes by a loudness mapping circuit LM1, LM2, LM3, or LM4. Loudness mapping is a critical element in the adjustment of the speech processor so that the loudness relations within and between speech sounds are preserved on each electrode. The preferred loudness mapping function is achieved by establishing a linear or logarithmic function between the acoustic and electrical amplitudes. The selected function is chosen to define, for each stimulation site, the amplitudes of the electrical stimulation that produce a signal that is at least equal to the threshold sensation, but not greater than the maximal comfortable loudness, over the anticipated dynamic range of the acoustic signal. The loudness mapping circuits LM1, LM2, LM3, and LM4 may thus be realized by a circuit or program that provides a transfer function that generates an output signal that is always in the range between threshold and maximal loudness. Such circuits or programs are known in the art, and may range from a simple circuit that uses a P-N junction (diode or transistor) that is properly biased, to more complex circuits that involve numerous active filters and operational amplifiers, or DSP (digital signal processing) circuits that effectively provide a look-up table, or equivalent program-driven means for defining the desired loudness-mapping relationship.

Once the signal has been appropriately mapped to convert the acoustical amplitude to an appropriate electrical signal amplitude, biphasic pulses having the determined electrical amplitude are then generated using a continuous interleaved sampling (CIS) technique. A biphasic pulse is one that has a short pulse of one polarity followed immediately (or almost immediately, e.g., within a few microseconds) by an opposite-polarity pulse of the same magnitude (width and amplitude). The CIS strategy stipulates that only one signal be sampled at any instant of time. However, the sampling rates may be very rapid, e.g, from 250 to 5000 Hz, with sampling pulse widths of from 10 to 250 μsec. To perform such sampling, a suitable oscillator/clock circuit 70 sets the basic sampling interval; and then an interleave pulse modulator 72 directs the sampled pulse to a gate or multiplier circuit 74–77 of one of the four channels.

It is noted that circuits that employ a CIS strategy as described above are known in the art. The present invention is not directed to just a CIS strategy, but is rather directed to a low-cost multichannel cochlear implant device/system that employs a fast CIS strategy. The narrow pulses associated with such a fast CIS strategy advantageously have their energy at a sufficiently high frequency to be amendable to inductive coupling through a pair of aligned coils on either side of the patient's skin. With such inductive coupling, it is thus possible to use the coupled energy directly as a stimulation pulse, without the need to generate, modulate, and demodulate a carrier signal, thereby allowing the implant device to be extremely simple consisting of just a coil having its ends connected through suitable wires to respective electrodes for each channel.

Figure 6:
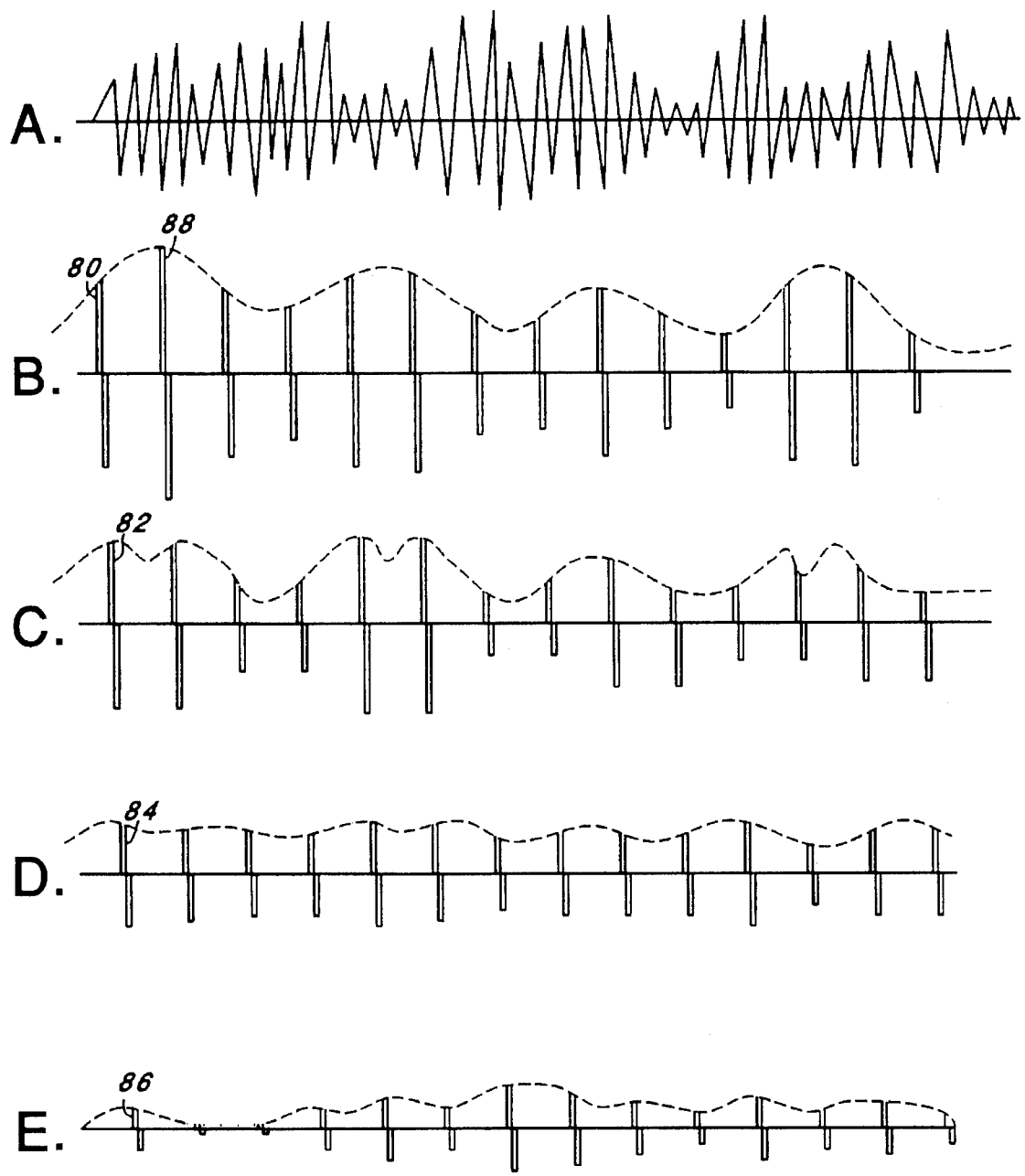
FIG. 6 is a timing waveform diagram that illustrates the concept of splitting the incoming speech signal into four bands, and sampling the signals of each band in an interleaved (non-simultaneous) fashion.

The above signal processing techniques, as well as the CIS processing strategy, are further described in connection with FIGS. 6 and 7. In FIG. 6, waveform A symbolically represents the incoming full-band signal that is sensed by the microphone 56 and processed by the preamplifier 60, pre-emphasis filter 62, and AGC circuit 64. The dotted line portion of waveforms "B", "C", "D" and "E" represent, for each channel, the instantaneous envelope waveforms obtained at the output the low pass filters LP1, LP2, LP3 and LP4, and as mapped using the loudness mapping circuits LM1, LM2, LM3 and LM4, respectively.

At a first instant of time, a first sample pulse 80 samples the "B" waveform (Channel 1) and determines its amplitude at the sample time. An appropriate biphasic sampling pulse of that amplitude is then generated. At the next sampling time, a second sample pulse 82 samples the "C" waveform (Channel 2) and determines its amplitude at the sample time, generating a corresponding biphasic sampling pulse. At the next sampling time, a third sample pulse 84 samples the waveform (Channel 3) and determines its amplitude at the sample time, generating a corresponding biphasic sampling pulse. At the next sampling time, a fourth sample pulse 86 samples the "E" waveform (Channel 4) and determines its amplitude at the sample time, generating a corresponding biphasic sampling pulse. At the next sampling time, a fifth sample pulse 88 samples the waveform (Channel 1) again, and the process continues in this manner, with one channel being sampled each sampling time, and with each channel being sampled every fourth sampling time.

It should be pointed out that that which is shown in FIG. 6 is not necessarily drawn to scale, particularly relative to the time (horizontal) axis. In the CIS strategy employed, the sampling occurs at a very rapid rate relative to the signal rates in the waveform(s) that is being sampled. Hence, if FIG. 6 were drawn appropriately, the sampling pulses would likely be much narrower than shown, and much closer together.

FIG. 7 shows the results, on an expanded scale, of applying a CIS strategy to a 4 channel system. A biphasic pulse 90 has an amplitude (both positive and negative) that is a function of the processed waveform (i.e., the band-limited signal that has been rectified, filtered, and mapped for loudness) at the time of sampling. The interchannel sampling time is "T". Thus, T seconds after the pulse 90 is generated, another biphasic pulse 92 is generated that has an amplitude determined by the sampled Channel 2 waveform. In a similar manner, biphasic pulses 94 and 96 are generated as a function of the amplitude of the sampled Channel 3 and Channel 4 waveforms, respectively. The process then repeats, with another biphasic pulse being generated for Channel 1 T seconds after the pulse 96, or 4T seconds after the last pulse for Channel 1.

Returning momentarily to FIG. 5, the biphasic pulses generated by the interleave pulse modulator 72, in combination with the multiplier/gate circuits 74–77, are applied to the coils 54 of the headpiece 22 via the cable 58. Preferably, a gain control device G1, G2, G3, and G4, is inserted in each line so that the overall amplitude of the biphasic stimulation pulses applied to that channel can be adjusted by the user, or an audiologist, to compensate for variations in skin thickness, etc. Such gain control device may be as simple as a potentiometer that attenuates the biphasic pulse by an amount controlled by a manual setting. More sophisticated gain control devices may also be used, such as active amplifier/driver circuits that include gain adjustment features.

When the biphasic pulse is applied to the appropriate coil 54 of the headpiece, it is coupled to the implanted coil 28 of the implantable array 12. Such coupling tends to smooth the waveform, as shown in the bottom portion of FIG. 7. Thus, the current resulting from application of the pulse 90 to one of the headpiece coils 54 causes a biphasic current pulse 100 to flow between the electrodes of the implantable array 12 connected to the particular coil 28 that is coupled to receive the pulse 90. In a similar fashion, biphasic current pulses 102–108 flow between appropriate electrodes of the implantable array 12 corresponding to application of the biphasic pulses 92–98, respectively, to the headpiece coils 54. Note that in every case the current at the electrodes is biphasic, and that only one current is applied to any pair of electrodes at any instant of time.

As described above, it is thus seen that the invention provides a low-cost, four-channel cochlear stimulation system. In a preferred embodiment, the system utilizes a completely passive, non-hermetically sealed, implantable electrode array having four electrodes, four receiving coils, and a reference electrode. The coils and electrodes may be made from a single type of biocompatible metal, and carried in a carrier of silicon rubber. One end of the carrier may be pre-formed in a spiral to match the basal turn of the cochlea, with the four electrodes being spaced apart along the inner radius of the spiral.

It is further seen that the invention provides an inexpensive cochlear stimulation system that offers the best combination of reliability, low cost and robust medical properties for widespread application. The invention thus has widespread application in underdeveloped areas, requiring minimal medical supervision and attention once implanted.

It is also seen that the invention provides an inexpensive cochlear stimulation system that utilizes the frequency content of brief biphasic pulses generated in multiple channels of a CIS (or equivalent) processing strategy to permit such pulses to be inductively coupled through the skin of a patient to an aligned implanted coil with reasonable efficiency. Such pulses are then used directly as a stimulating signal at electrodes connected to the implanted coil without the need for intervening implanted electrical or electronic circuitry.

It is additionally seen that the invention provides such a low-cost cochlear stimulation system wherein the implantable portion thereof need not be hermetically sealed, where all components may be made from biocompatible materials, and where the usable life of the implantable portion is designed to exceed that of the patient within whom it is implanted.

While the invention herein disclosed has been described by means of specific embodiments and applications thereof, numerous modifications and variations could be made thereto by those skilled in the art without departing from the scope of the invention set forth in the claims.

What is claimed is:

1. A low-cost, multichannel cochlear stimulation system comprising:

a passive, non-hermetically sealed, implantable receiver/electrode array comprising:
   a carrier in which is embedded a plurality of coil assemblies at a proximal end of the carrier and a plurality of electrodes at a distal end of the carrier, the distal and proximal ends of the carrier being integrally connected together, the distal end of the carrier being adapted for insertion into a human cochlea, whereby the plurality of electrodes may be placed within the cochlea,
   the proximal end of the carrier holding the plurality of coil assemblies in a predetermined pattern,
   the plurality of coil assemblies and electrodes comprising the only electrical components within the carrier, the coil assemblies each comprising a sufficient number of turns of a first wire wound to form a coil, one end of the first wire of each coil being electrically connected directly to at least one of the electrodes at the distal end of the carrier and an other end of the first wire of each coil being connected directly to a second electrode, and
   implantable alignment means for aligning the plurality of coil assemblies with corresponding external coils; and an external wearable processor comprising:
   microphone means for generating an electrical signal representative of sensed audible sounds,
   filter means for dividing the electrical signal into a plurality of frequency bands, thereby creating a corresponding plurality of frequency band signals, the number of frequency bands being the same as the number of implanted coil assemblies, whereby there is an implanted coil assembly for each frequency band,
   signal processing means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than 250 μsec and a repetition rate of at least 250 Hz,
   an external headpiece having a plurality of external coils, each connected to receive the biphasic stimulation signal of one of the plurality of frequency bands, and
   external alignment means for aligning each of the external coils of the external headpiece with respective ones of the plurality of coil assemblies of the implantable receiver/electrode array;

whereby the narrow biphasic stimulation pulses received by each of the plurality of external coils are inductively coupled to respective ones of the plurality of implantable coil assemblies, thereby causing an induced biphasic stimulation current to appear at respective ones of the implantable electrodes as a function of sensed audible sounds.

2. The cochlear stimulation system of claim 1 wherein the narrow biphasic stimulation pulses produced by the signal processing means have a width of less than approximately 100 μsec and a repetition rate of at least 500 Hz.

3. The cochlear stimulation system of claim 1 wherein the number of coil assemblies within the implantable receiver/electrode array and the number of frequency bands into which the filter means of the wearable processor divides the electrical signal comprises four.

4. The cochlear stimulation system of claim 3 wherein the four frequency bands comprise a low frequency band for frequencies up to approximately 700 Hz, a first intermediate frequency band for frequencies between approximately 700 Hz and 1400 Hz, a second intermediate frequency band for frequencies between approximately 1400 Hz and 2800 Hz, and an upper frequency band for frequencies greater than approximately 2800 Hz.

5. The cochlear stimulation system of claim 1 wherein the external alignment means comprises at least one permanent magnet mounted within the external headpiece, and the implantable alignment means includes at least one magnetic member embedded within the carrier.

6. The cochlear stimulation system of claim 1 wherein the microphone means of the external wearable processor comprises
   a microphone, a preamplifier coupled to the microphone, pre-emphasis filter means for equalizing the energy content of an output signal received from the preamplifier, and automatic gain control means for adjusting an output signal from the pre-emphasis filter means to compensate for differences in loudness of different audible sounds sensed by the microphone.

7. The cochlear stimulation system of claim 1 wherein the signal processing means within the external wearable processor includes a plurality of rectifier circuits for rectifying the corresponding frequency band signals; and a plurality of low pass filter means connected to receive an output from one of the plurality of rectifier circuits, respectively, for deriving an instantaneous envelope signal of the content of the respective frequency band signals.

8. The cochlear stimulation system of claim 7 wherein the signal processing means within the external wearable processor further includes means for sampling the instantaneous envelope signal of the respective frequency band signals, and mapping the sampled signal to an appropriate biphasic stimulation amplitude, on a continuous interleaved sampled (CIS) basis, with only one envelope signal being sampled, and hence with only one biphasic stimulation signal being generated, at any instant of time.

9. The cochlear stimulation system of claim 8 further including loudness mapping means coupled to the means for sampling and mapping for applying a logarithmic function between the instantaneous envelope signal and the biphasic stimulation amplitude of the resulting biphasic stimulation signal.

10. The cochlear stimulation system of claim 1 wherein the carrier comprises an elongate carrier made from silicone rubber.

11. The cochlear stimulation system of claim 10 wherein the distal end of the carrier is formed in the shape of a spiral to match the basal turn of a human cochlea, with the plurality of electrodes being spaced apart along an inner radius of the spiral.

12. The cochlear stimulation system of claim 1 wherein a first end of the first wire from which the coil of each coil assembly is made is bonded to a second biocompatible wire that extends the length of the carrier inside of the carrier to a respective electrode at the distal end of the carrier.

13. The cochlear stimulation system of claim 12 wherein each electrode at the distal end of the carrier comprises a ball formed at a distal end of the second biocompatible wire, a portion of which ball is exposed through the surface of the carrier.

14. The cochlear stimulation system of claim 13 wherein the second wire is made from approximately 90% platinum and 10% iridium.

15. The cochlear stimulation system of claim 1 wherein a second end of the first wire from which the coil of each coil assembly is made is bonded to a third biocompatible wire that extends to another electrode exposed at the surface of the carrier.

16. The cochlear stimulation system of claim 15 wherein the third wire is made from approximately 90% platinum and 10% iridium.

17. A low-cost, four-channel cochlear stimulation system comprising:

a passive, non-hermetically sealed, implantable receiver/electrode array; and an external wearable processor;

wherein the implantable receiver/electrode array consists of:

an elongate carrier in which is embedded four coil assemblies at a proximal end of the carrier and four electrodes at a distal end of the carrier, with the distal end of the carrier being formed to fit within a human cochlea, and with the proximal end of the carrier holding the four coil assemblies in a predetermined pattern, and implantable alignment means for aligning the plurality of coil assemblies with corresponding external coils, and wherein each coil assembly comprises a multiplicity of turns of a first wire wound to form a coil, with a first end of the first wire of each coil being bonded to a second wire that extends the length of the elongate carrier inside of the carrier to a respective electrode at the distal end of the carrier, and with a second end of the first wire of each coil being bonded to a third wire that extends to another electrode exposed at the surface of the carrier, and wherein the second and third wires are each made from a biocompatible conductive material, and further wherein each electrode comprises a ball formed from the wire extending thereto, with a portion of the ball being exposed through the surface of the carrier; and wherein the external wearable processor comprises:

microphone means for generating an electrical signal representative of sensed audible sounds, filter means for dividing the electrical signal into four frequency bands, thereby creating four corresponding frequency band signals, whereby there is an implanted coil assembly and corresponding electrode for each frequency band, a signal processor that includes means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than 250 μsec and a repetition rate of at least 250 Hz, and an external headpiece having four external coils, each connected to receive one of the respective biphasic stimulation signals, external alignment means for positioning the external headpiece in alignment with the implantable alignment means to align each of the external coils of the external headpiece with respective ones of the plurality of coil assemblies of the implantable receiver/electrode array;

whereby the narrow biphasic stimulation pulses received by each of the four external coils are inductively coupled to respective ones of the four implantable coil assemblies, thereby causing an induced biphasic stimulation current to appear at respective ones of the implantable electrodes as a function of sensed audible sounds.

18. A passive, non-hermetically sealed, implantable receiver/electrode array for use with a four-channel cochlear stimulation system consisting of:

a carrier in which is embedded four coil assemblies at a proximal end of the carrier and four electrodes at a distal end of the carrier, with the distal end of the carrier being formed to fit within a human cochlea, and with the proximal end of the carrier holding the four coil assemblies in a predetermined pattern, and implantable alignment means for aligning the plurality of coil assemblies with corresponding external coils, and wherein each coil assembly comprises a multiplicity of turns of a first wire wound to form a coil, with a first end of the first wire of each coil being bonded to a second wire that extends the length of the carrier inside of the carrier to a respective electrode at the distal end of the carrier, and with a second end of the first wire of each coil being bonded to a third wire that extends to another electrode exposed at the surface of the carrier, and wherein the second and third wires are each made from a biocompatible conductive material, and further wherein each electrode comprises a ball formed from the wire extending thereto, with a portion of the ball being exposed through the surface of the carrier.

19. A method of directly stimulating a human cochlea with electrical signals representative of sensed audio sounds, thereby imparting the sensation of hearing to a deaf patient, the method comprising the steps of:

(a) implanting a receiver/electrode array into the patient, the receiver/electrode array comprising a non-hermetically sealed carrier in which is embedded a plurality of coil assemblies at a proximal end of the carrier and a corresponding plurality of electrodes at a distal end of the carrier, with each electrode at the distal end of the carrier being electrically connected to a respective one of the coil assemblies at the proximal end of the carrier, and with the distal end of the carrier being inserted into the human cochlea, and with the proximal end of the carrier being positioned just beneath the skin of the patient above an ear of the patient;

(b) generating an electrical signal representative of sensed audible sounds, (c) dividing the electrical signal into a plurality of frequency bands, the plurality of frequency bands being the same number as the plurality of implanted coil assemblies within the receiver/electrode array, whereby there is an implanted coil assembly and corresponding electrode for each frequency band, (d) processing each of the plurality of frequency band signals to produce a biphasic stimulation signal for each frequency band, the biphasic stimulation signal comprising a series of narrow biphasic stimulation pulses of varying amplitude having a width of less than 100 μsec and a repetition rate of at least 500 Hz, and (e) applying the biphasic stimulation signal of each frequency band to a respective external coil;

(f) aligning each of the plurality of external coils with a corresponding one of the plurality of implanted coil assemblies such that there is a distance at least equal to the thickness of the patient's skin separating the external coils from the implanted coil assemblies, whereby the narrow biphasic stimulation pulses received by each of the plurality of external coils are inductively coupled to respective ones of the plurality of coil assemblies, thereby inducing a biphasic stimulation current in the implanted coil assemblies that appears at a respective one of the electrodes at the distal end of the carrier as a function of sensed audible sounds.

20. A low-cost, multichannel cochlear stimulation system comprising:

a passive, non-hermetically sealed, implantable receiver/electrode array comprising:
a carrier in which is embedded a plurality of coil assemblies at a proximal end of the carrier and a corresponding plurality of electrodes at a distal end of the carrier, the distal end of the carrier being adapted for insertion into a human cochlea, whereby the plurality of electrodes are placed within the cochlea,
the proximal end of the carrier holding the plurality of coil assemblies in a predetermined pattern,
the coil assemblies each comprising a sufficient number of turns of a first wire wound to form a coil, one end of each coil being electrically connected directly to at least one of the electrodes at the distal end of the carrier and an other end of each coil being connected directly to a second electrode, and
implantable alignment means for aligning the plurality of coil assemblies with corresponding external coils; and an external wearable processor comprising:
microphone means for generating an electrical signal representative of sensed audible sounds,
filter means for dividing the electrical signal into a plurality of frequency bands, thereby creating a corresponding plurality of frequency band signals, the number of frequency bands being the same as the number of implanted coil assemblies, whereby there is an implanted coil assembly for each frequency band,
signal processing means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than approximately 50 μsec and a repetition rate of at least 1000 Hz,
an external headpiece having a plurality of external coils, each connected to receive the biphasic stimulation signal of one of the plurality of frequency bands, and
external alignment means for aligning each of the external coils of the external headpiece with respective ones of the plurality of coil assemblies of the implantable receiver/electrode array;
whereby the narrow biphasic stimulation pulses received by each of the plurality of external coils are inductively coupled to respective ones of the plurality of implantable coil assemblies, thereby causing an induced biphasic stimulation current to appear at respective ones of the implantable electrodes as a function of sensed audible sounds.

21. The cochlear stimulation system of claim 20 wherein the prescribed signal processing strategy comprises a continuous interleaved sampling (CIS) strategy wherein only one biphasic stimulation pulse is produced at any given time.

22. The cochlear stimulation system of claim 20 wherein the number of coil assemblies within the implantable receiver/electrode array and the number of frequency bands into which the filter means of the wearable processor divides the electrical signal comprises four.

23. The cochlear stimulation system of claim 22 wherein the four frequency bands comprise a low frequency band for frequencies up to approximately 700 Hz, a first intermediate frequency band for frequencies between approximately 700 Hz and 1400 Hz, a second intermediate frequency band for frequencies between approximately 1400 Hz and 2800 Hz, and an upper frequency band for frequencies greater than approximately 2800 Hz.

24. The cochlear stimulation system of claim 20 wherein the external alignment means comprises at least one permanent magnet mounted within the external headpiece, and the implantable alignment means includes at least one magnetic member embedded within the carrier.

25. The cochlear stimulation system of claim 20 wherein the microphone means of the external wearable processor comprises a microphone, a preamplifier coupled to the microphone, pre-emphasis filter means for equalizing the energy content of an output signal received from the preamplifier, and automatic gain control means for adjusting an output signal from the pre-emphasis filter means to compensate for differences in loudness of different audible sounds sensed by the microphone.

26. The cochlear stimulation system of claim 20 wherein the signal processing means includes a plurality of rectifier circuits for rectifying the corresponding frequency band signals; and a plurality of low pass filter means connected to receive an output from one of the plurality of rectifier circuits, respectively, for deriving an instantaneous envelope signal of the content of the respective frequency band signals.

27. The cochlear stimulation system of claim 26 wherein the signal processing means further includes means for sampling the instantaneous envelope signal of the respective frequency band signals, and mapping the sampled signal to an appropriate biphasic stimulation amplitude, on a continuous interleaved sampled (CIS) basis, with only one envelope signal being sampled, and hence with only one biphasic stimulation signal being generated, at any instant of time.

28. A low-cost, multichannel cochlear stimulation system comprising:

a passive, non-hermetically sealed, implantable receiver/ electrode array comprising:

a carrier in which is embedded a plurality of coil assemblies at a proximal end of the carrier and a corresponding plurality of electrodes at a distal end of the carrier, the distal end of the carrier being adapted for insertion into a human cochlea, whereby the plurality of electrodes are placed within the cochlea, the proximal end of the carrier holding the plurality of coil assemblies in a predetermined pattern, the coil assemblies each comprising a sufficient number of turns of a first wire wound to form a coil, one end of each coil being electrically connected directly to at least one of the electrodes at the distal end of the carrier and an other end of each coil being connected directly to a second electrode, and implantable alignment means for aligning the plurality of coil assemblies with corresponding external coils; and an external wearable processor comprising:

microphone means for generating an electrical signal representative of sensed audible sounds, filter means for dividing the electrical signal into a plurality of frequency bands, thereby creating a corresponding plurality of frequency band signals, the number of frequency bands being the same as the number of implanted coil assemblies, whereby there is an implanted coil assembly for each frequency band, signal processing means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than 250 μsec and a repetition rate of at least 250 Hz, the signal processing means comprising a plurality of rectifier circuits for rectifying the corresponding frequency band signals, a plurality of low pass filter means connected to receive an output from one of the plurality of rectifier circuits, respectively, for deriving an instantaneous envelope signal of the content of the respective frequency band signals, means for sampling the instantaneous envelope signal of the respective frequency band signals, and mapping the sampled signal to an appropriate biphasic stimulation amplitude, on a continuous interleaved sampled (CIS) basis, with only one envelope signal being sampled, and hence with only one biphasic stimulation signal being generated, at any instant of time, and loudness mapping means coupled to the means for sampling and mapping for applying a linear function between the instantaneous envelope signal and the biphasic stimulation amplitude of the resulting biphasic stimulation signal, an external headpiece having a plurality of external coils, each connected to receive the biphasic stimulation signal of one of the plurality of frequency bands, and external alignment means for aligning each of the external coils of the external headpiece with respective ones of the plurality of coil assemblies of the implantable receiver/electrode array;

whereby the narrow biphasic stimulation pulses received by each of the plurality of external coils are inductively coupled to respective ones of the plurality of implantable coil assemblies, thereby causing an induced biphasic stimulation current to appear at respective ones of the implantable electrodes as a function of sensed audible sounds.

29. A low-cost, multichannel cochlear stimulation system comprising:

a passive, non-hermetically sealed, implantable receiver/ electrode array comprising:

a carrier in which is embedded a plurality of coil assemblies at a proximal end of the carrier and a plurality of electrodes at a distal end of the carrier, the distal end of the carrier being adapted for insertion into a human cochlea, whereby the plurality of electrodes are placed within the cochlea, the proximal end of the carrier holding the plurality of coil assemblies in a predetermined pattern, the coil assemblies each comprising a sufficient number of turns of a first wire wound to form a coil, one end of each coil being electrically connected directly to at least one of the plurality of electrodes at the distal end of the carrier and an other end of each coil being connected directly to a second electrode; and an external wearable processor comprising:

microphone means for generating an electrical signal representative of sensed audible sounds, filter means for dividing the electrical signal into a plurality of frequency bands, thereby creating a corresponding plurality of frequency band signals, the number of frequency bands being the same as the number of implanted coil assemblies, whereby there is an implanted coil assembly for each frequency band, signal processing means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than approximately 50 μsec and a repetition rate of at least 1000 Hz, an external headpiece having a plurality of external coils, each connected to receive the biphasic stimulation signal of one of the plurality of frequency bands, and external alignment means for aligning each of the external coils of the external headpiece with respective ones of the plurality of coil assemblies of the implantable receiver/electrode array;

whereby the narrow biphasic stimulation pulses received by each of the plurality of external coils are inductively coupled to respective ones of the plurality of implantable coil assemblies, thereby causing an induced biphasic stimulation current to appear at respective ones of the implantable electrodes as a function of sensed audible sounds.

30. A low-cost, multichannel cochlear stimulation system comprising:

a passive, non-hermetically sealed, implantable receiver/electrode array comprising:

a carrier in which is embedded a plurality of coil assemblies at a proximal end of the carrier and a plurality of electrodes at a distal end of the carrier, the distal end of the carrier being adapted for insertion into a human cochlea, whereby the plurality of electrodes are placed within the cochlea, the proximal end of the carrier holding the plurality of coil assemblies in a predetermined pattern, the coil assemblies each comprising a sufficient number of turns of a first wire wound to form a coil, one end of each coil being electrically connected directly to at least one of the plurality of electrodes at the distal end of the carrier and an other end of each coil being connected directly to a second electrode; and an external wearable processor comprising:

microphone means for generating an electrical signal representative of sensed audible sounds, filter means for dividing the electrical signal into a plurality of frequency bands, thereby creating a corresponding plurality of frequency band signals, the number of frequency bands being the same as the number of implanted coil assemblies, whereby there is an implanted coil assembly for each frequency band, signal processing means for processing each of the plurality of frequency band signals in accordance with a prescribed speech processing strategy to produce a biphasic stimulation signal for each frequency band, the biphasic stimulation signal comprising a series of narrow biphasic stimulation pulses of varying amplitude having a width of less than 250 μsec and a repetition rate of at least 250 Hz, the signal processing means comprising a plurality of rectifier circuits for rectifying the corresponding frequency band signals, a plurality of low pass filter means connected to receive an output from one of the plurality of rectifier circuits, respectively, for deriving an instantaneous envelope signal of the content of the respective frequency band signals, means for sampling the instantaneous envelope signal of the respective frequency band signals, and mapping the sampled signal to an appropriate biphasic stimulation amplitude, on a continuous interleaved sampled (CIS) basis, with only one envelope signal being sampled, and hence with only one biphasic stimulation signal being generated, at any instant of time, and loudness mapping means coupled to the means for sampling and mapping for applying a linear function between the instantaneous envelope signal and the biphasic stimulation amplitude of the resulting biphasic stimulation signal, an external headpiece having a plurality of external coils, each connected to receive the biphasic stimulation signal of one of the plurality of frequency bands, and external alignment means for aligning each of the external coils of the external headpiece with respective ones of the plurality of coil assemblies of the implantable receiver/electrode array;

whereby the narrow biphasic stimulation pulses received by each of the plurality of external coils are inductively coupled to respective ones of the plurality of implantable coil assemblies, thereby causing an induced biphasic stimulation current to appear at respective ones of the implantable electrodes as a function of sensed audible sounds.

\* \* \* \* \*